United States Patent
Harari et al.

(10) Patent No.: US 10,692,874 B2
(45) Date of Patent: Jun. 23, 2020

(54) 3-DIMENSIONAL NOR STRING ARRAYS IN SEGMENTED STACKS

(71) Applicant: Sunrise Memory Corporation, Los Gatos, CA (US)

(72) Inventors: Eli Harari, Saratoga, CA (US); Wu-Yi Chien, San Jose, CA (US)

(73) Assignee: SUNRISE MEMORY CORPORATION, Fremont, CA (US)

( * ) Notice: Subject to any disclaimer, the term of this patent is extended or adjusted under 35 U.S.C. 154(b) by 0 days.

(21) Appl. No.: 16/006,573

(22) Filed: Jun. 12, 2018

(65) Prior Publication Data

US 2018/0366471 A1     Dec. 20, 2018

Related U.S. Application Data

(60) Provisional application No. 62/522,661, filed on Jun. 20, 2017.

(51) Int. Cl.
| | |
|---|---|
| *H01L 27/115* | (2017.01) |
| *G11C 16/04* | (2006.01) |
| *H01L 23/528* | (2006.01) |
| *H01L 27/11556* | (2017.01) |
| *H01L 27/11521* | (2017.01) |

(52) U.S. Cl.
CPC .......... *H01L 27/115* (2013.01); *G11C 16/04* (2013.01); *H01L 23/528* (2013.01); *H01L 27/11521* (2013.01); *H01L 27/11556* (2013.01)

(58) Field of Classification Search
CPC ............ H01L 27/115; H01L 27/11521; H01L 27/11556; H01L 23/528; H01L 27/11578; H01L 27/11568; H01L 27/11563; G11C 16/04

See application file for complete search history.

(56) References Cited

U.S. PATENT DOCUMENTS

| | | | |
|---|---|---|---|
| 6,040,605 A | 3/2000 | Sano et al. | |
| 6,434,053 B1 | 8/2002 | Fujiwara | |
| 6,580,124 B1 | 6/2003 | Cleeves et al. | |
| 6,744,094 B2 | 6/2004 | Forbes | |
| 6,946,703 B2 | 9/2005 | Ryu et al. | |
| 8,630,114 B2 | 1/2014 | Lue | |
| 10,074,667 B1 * | 9/2018 | Higashi | H01L 23/481 |
| 2001/0053092 A1 | 12/2001 | Kosaka et al. | |
| 2004/0246807 A1 | 12/2004 | Lee | |

(Continued)

OTHER PUBLICATIONS

"PCT Search Report and Written Opinion, PCT/US2018/038373", dated Sep. 10, 2018.

*Primary Examiner* — Thanhha S Pham
(74) *Attorney, Agent, or Firm* — Edward C. Kwok; VLP Law Group, LLP

(57) ABSTRACT

A memory structure formed above a semiconductor substrate includes two or more modules each formed on top of each other separated by a layer of global interconnect conductors. Each memory module may include a 3-dimensional array of memory transistors organized as NOR array strings. Each 3-dimensional array of memory transistors is provided vertical local word lines as gate electrodes to the memory transistors. These vertical local word lines are connected by the layers of global interconnect conductors below and above the 3-dimensional array of memory transistors to circuitry formed in the semiconductor substrate.

4 Claims, 3 Drawing Sheets

(56) References Cited

U.S. PATENT DOCUMENTS

| | | |
|---|---|---|
| 2005/0128815 A1 | 6/2005 | Ishikawa et al. |
| 2006/0155921 A1 | 7/2006 | Gorobets et al. |
| 2009/0157946 A1 | 6/2009 | Arya |
| 2011/0208905 A1 | 8/2011 | Shaeffer et al. |
| 2013/0256780 A1 | 10/2013 | Kai et al. |
| 2014/0117366 A1 | 5/2014 | Saitoh |
| 2014/0340952 A1* | 11/2014 | Ramaswamy ........ G11C 11/221 365/51 |
| 2016/0314042 A1 | 10/2016 | Plants |
| 2017/0092370 A1 | 3/2017 | Harari |

* cited by examiner

KEY TO

3-DIMENSIONAL NOR STRING ARRAYS IN SEGMENTED STACKS

CROSS REFERENCES TO RELATED APPLICATIONS

This application is related to and claims priority of U.S. provisional application ("Provisional Application"), Ser. No. 62/552,661, entitled "3-Dimensional NOR String Arrays in Segmented Stacks," filed on Jun. 20, 2017. This application is related to copending U.S. patent application ("Copending Non-provisional application"), Ser. No. 15/248,420, entitled "Capacitive-Coupled Non-Volatile Thin-film Transistor Strings in Three-Dimensional Arrays," filed Aug. 26, 2016. The Provisional Application and the Copending Non-provisional application are hereby incorporated by reference in their entireties.

BACKGROUND OF THE INVENTION

1. Field of the Invention

The present invention relates to non-volatile NOR-type memory strings. In particular, the present invention relates to manufacturing processes for forming non-volatile NOR-type memory strings in a 3-dimensional semiconductor structure.

2. Discussion of the Related Art

In the Copending application, FIGS. 2i, 2i-1, 2j, 2k, and 2k-1 show three-dimensional memory structures in which the NOR strings are formed out of stacks of active strips, with each active strip being formed out of multiple layers of semiconductor material. Typically, in such a memory structure, there may be 4, 8, 16, 32 or more active layers. See, e.g., in FIG. 2i of the Copending Non-provisional application, reproduced herein as FIG. 1, two vertically stacked active layers 202-6 and 202-7, isolated from each other by isolation layer 203-7 are each provided to form multiple NOR strings. As shown in FIG. 1, each of active layers 202-6 and 202-7 includes semiconductor layers 221-223. With the large number of active layers, the resulting stack can be exceedingly tall, making it challenging to anisotropically etch narrow trenches all the way down to the bottom of the memory structure, underneath which is a semiconductor substrate at which support circuits (e.g., sense amplifiers and decoders) are often formed. Furthermore, the resulting tall and narrow stacks may be mechanically unstable, requiring supporting struts or structures. Additionally, the vertical local word-lines (e.g., word lines 208W-s and 208W-a in FIG. 1)—which are formed inside these long and narrow trenches—present high resistance R and large RC time constants which delay the response time for addressed memory strings that are furthest away from global word lines 208g-a and 208g-s.

The tall and narrow anisotropically etched trenches may be mitigated by using a segmented stack technique, which is used in recent years in horizontal NAND strings. One example of the segmented stack technique is disclosed in the article ("Kim"), "Multi-layered Vertical Gate NAND Flash Overcoming Stacking Limit for Terabit Density Storage," by W. Kim et. al., published in the 2009 Symposium on VLSI Tech., Dig. Of technical papers, pp 188-189. However, the multi-layered NOR strings, such as those shown in the Copending Non-provisional application, require a different interconnect scheme than the interconnect scheme of the NAND strings in the Kim article.

SUMMARY

According to one embodiment of the present invention, a memory structure formed above a semiconductor substrate includes two or more modules each formed on top of each other separated by a layer of global interconnect conductors. Each memory module may include a 3-dimensional array of memory transistors organized as NOR array strings. Each 3-dimensional array of memory transistors is provided vertical local word lines as gate electrodes to the memory transistors. These vertical local word lines are connected by the layers of global interconnect conductors below and above the 3-dimensional array of memory transistors to circuitry formed in the semiconductor substrate.

More specifically, according to one embodiment of the present invention, a memory structure includes: (a) a semiconductor substrate having a planar surface, the semiconductor substrate having circuitry formed therein and thereon; (b) memory modules provided one on top of another above the planar surface, wherein each memory module includes: (i) two or more stacks of active strips each being spaced from another along a first direction substantially parallel the planar surface, each active strip running lengthwise along a second direction that is also substantially parallel the planar surface but orthogonal to the first direction, the active strips within each stack being provided one on top of another along a third direction that is substantially perpendicular to the planar surface, each active strip being formed out of semiconductor layers that provide drain, source and channel regions of thin-film storage transistors organized as NOR strings; (ii) a set of local word line conductors each running along the third direction to provide as gate electrodes to storage transistors provided in a designated one of the stacks of active strips; (iii) a first set of global word line conductors provided below the stacks of active strips, being spaced from each other along the second direction and each running lengthwise along the first direction, connecting the substrate circuitry to some of the local word lines; and (iv) a second set of global word line conductors provided above the stacks of active strips, being spaced from each other along the second direction and each running lengthwise along the first direction, connecting the substrate circuitry to some of the local word lines, wherein the second set of global word line conductors of each memory module, except for one memory module, is provided also as the first set of global word line conductors of another memory module located immediately above it.

The present invention is better understood upon consideration of the detailed description below in conjunction with the accompanying drawings.

DETAILED DESCRIPTION OF THE PREFERRED EMBODIMENTS

Figure 1:
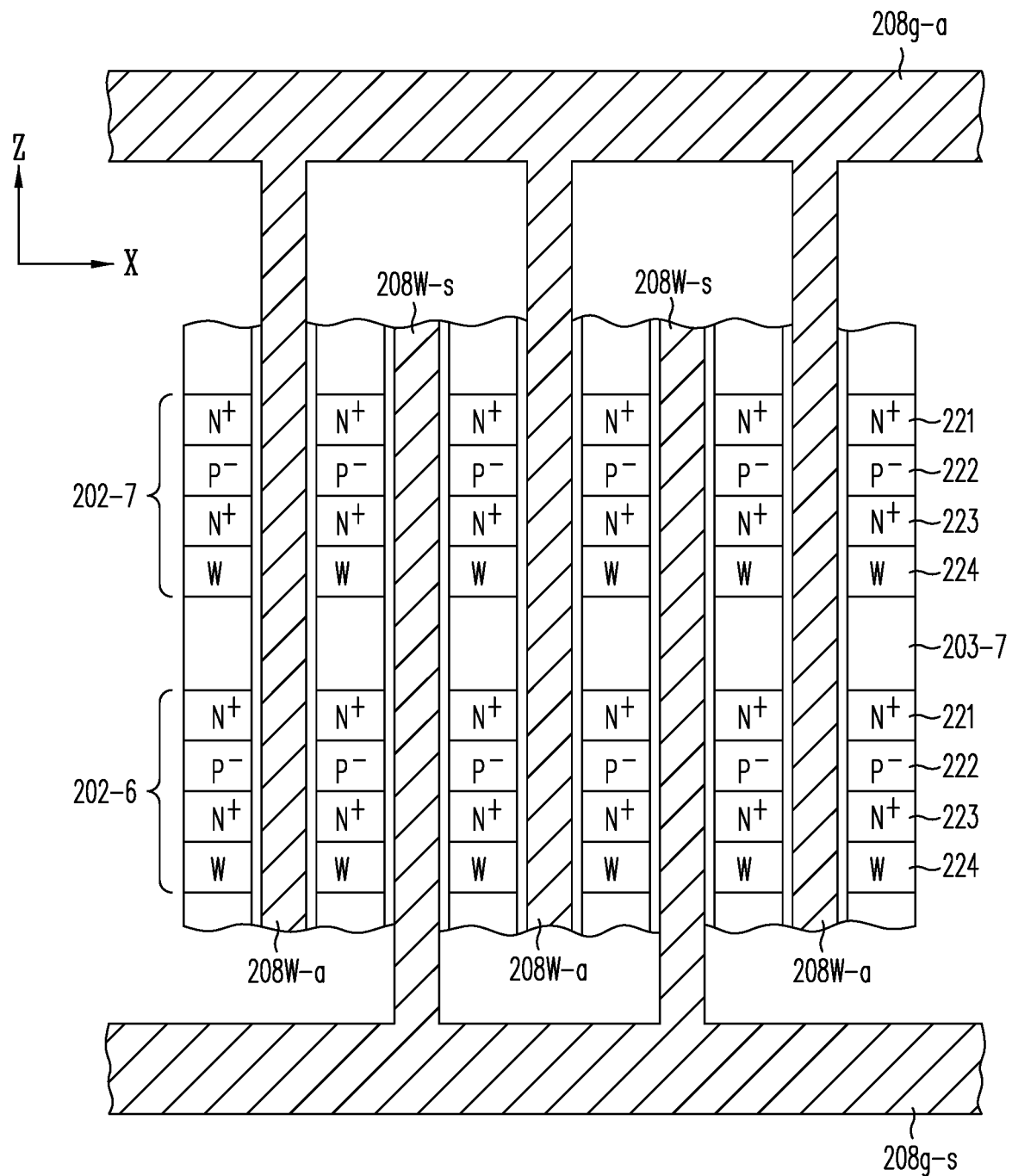
FIG. 1 reproduces FIG. 2i of the Copending Non-provisional application, showing two vertically stacked active layers 202-6 and 202-7, each provided to form multiple NOR strings out of semiconductor layers 221-223.

As shown in FIG. 1, each side edge of each active strip (e.g., active strip 202-7 or 202-8) in each active stack form a NOR string including memory transistors that are each accessed by a local word line (e.g., local word line 208W-a or 208W-s). Each local word line may be connected to circuitry in the semiconductor substrate through a global word line either from the top (e.g., global word lines 208g-a), or from the bottom (e.g., global word lines 208g-s). As shown in FIG. 1, the local word lines are shown to be connected through both top and bottom global word lines.

Figure 2A:
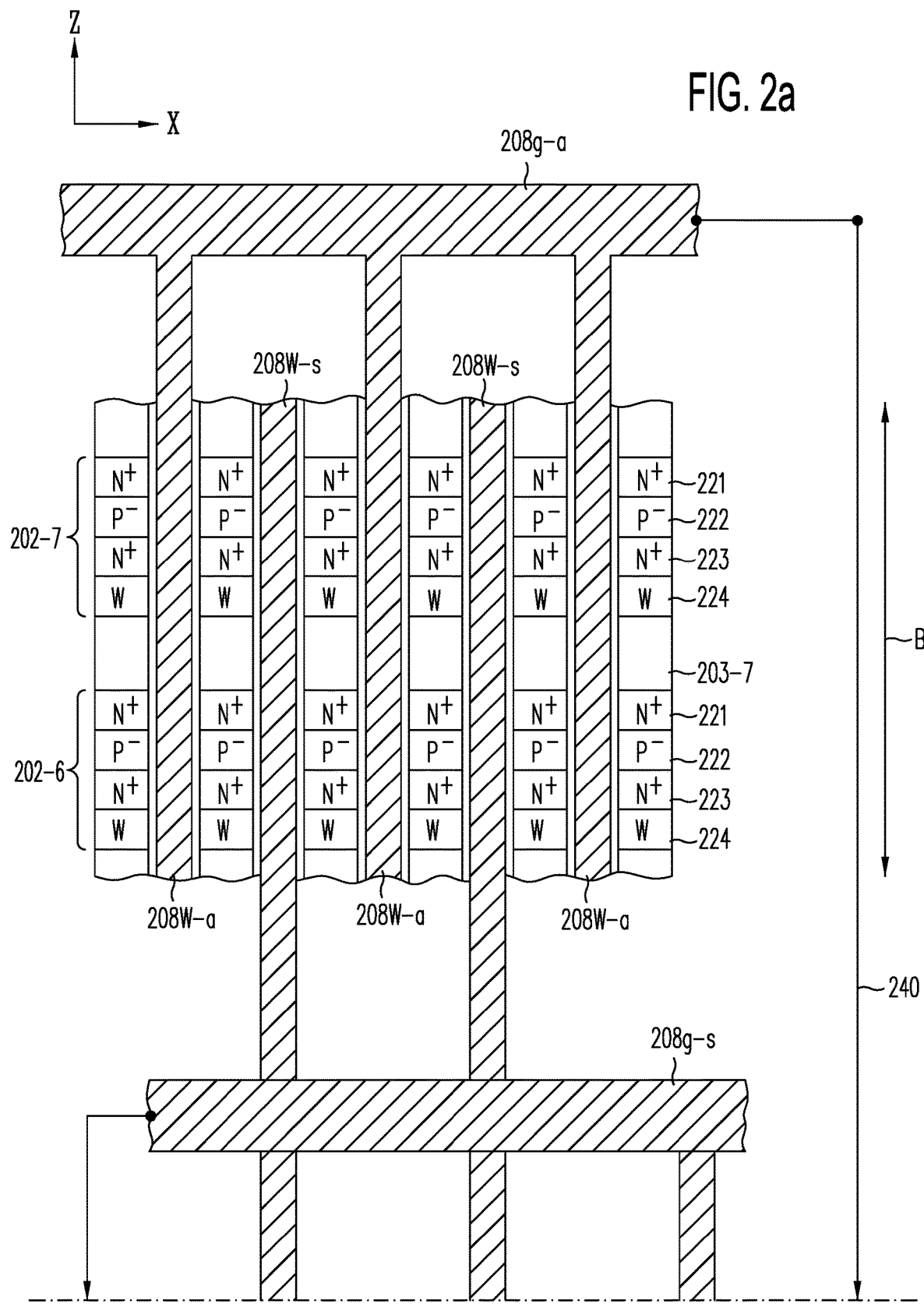
FIGS. 2a and 2b show active stacks each of at least four active strips being manufactured as two sets of half-height active stacks A and B, according to one embodiment of the present invention.
Figure 2B:
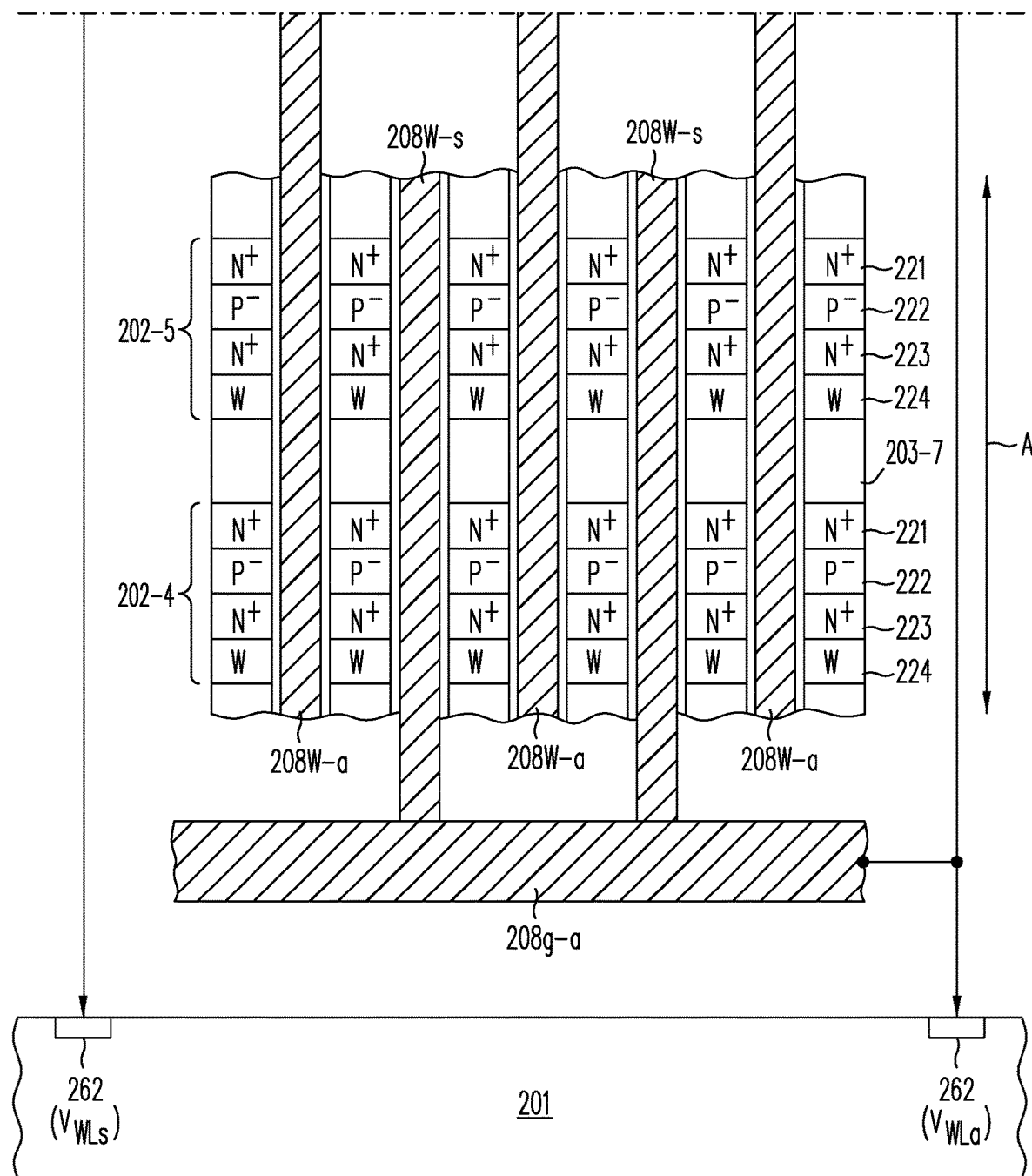
Figure 2:
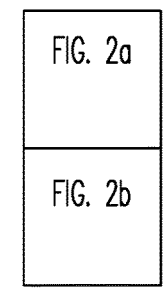

According to one embodiment of the present invention, to reduce the aspect ratio of the anisotropically etched deep trenches for local word lines 208W-a and 208W-s, and to reduce by almost half the resistance in each of these local word lines, the active stacks of the active strips in FIG. 1 may be manufactured as two or more sets of reduced-height active stacks. For example, FIG. 2 shows active stacks of at least four active strips being manufactured as two sets of half-height active stacks A and B, each active stack including two or more active strips formed therein, according to one embodiment of the present invention. In FIG. 2, half-height active stack A—which is shown to include at least active strips 202-4 and 202-5—are first formed, with local word lines 208W-a and 208W-s. Local word lines 208W-a and 208-s connect the circuitry (e.g., voltage sources $V_{WLs}$ and $V_{WLa}$) in semiconductor substrate 201 through global word lines 208g-a and global word lines 208g-s. Half-height active stacks B—which includes active strips 202-6 and 202-7—are next formed out of active layers on top of global word lines 208g-s and share global word lines 208g-s with half-height stacks A to provide connection to the substrate circuitry. A further set of global conductors (i.e., global word lines 208g-a of half-height active strip stacks B) are next formed on top of the active layers 202-6 and 202-7 to connect the substrate circuitry to the word lines 208W-a of half-height active strip stacks B. Although this process flow involves an increased number of process steps, it substantially reduces the high aspect ratio in the etch steps and results in mechanically more sturdy structures.

The above detailed description is provided to illustrate the specific embodiments of the present invention and is not intended to be limiting. Numerous variations and modifications within the scope of the present invention are possible. The present invention is set forth by the accompanying claims.

We claim:

1. A memory structure, comprising:
    a semiconductor substrate having a planar surface, the semiconductor substrate having circuitry formed therein and thereon;
    first and second memory modules provided above the planar surface, the second memory module being provided on top of the first memory module, wherein each memory module comprises:
        a plurality of stacks of active strips, the stacks being spaced from each other along a first direction substantially parallel the planar surface, each active strip running lengthwise along a second direction that is also substantially parallel the planar surface but orthogonal to the first direction, the active strips within each stack being provided one on top of another along a third direction that is substantially perpendicular to the planar surface, each active strip comprising semiconductor layers that form drain, source and channel regions of thin-film storage transistors organized as NOR strings; and
        a set of local word line conductors each running along the third direction to provide as gate electrodes to storage transistors in a designated one of the stacks of active strips; and
    a first set of global word line conductors provided between the first memory module and the second memory module, wherein the global word line conductors in the first set of global word line conductors are (i) spaced from each other along the second direction and each running along the first direction, and (ii) each in direct contact with selected local word line conductors of both the first and second memory modules.

2. The memory structure of claim 1, further comprising a second set of global word line conductors and a third set of global word line conductors, formed above the second memory module and below the first memory module, respectively, wherein, within each of the second and third sets of global word line conductors, the global word line conductors are spaced from each other along the second direction and each running along the first direction, and wherein the global word line conductors of the second and third set of global conductors are each in direct contact with selected local word line conductors in the second memory module and the first memory module, respectively.

3. The memory structure of claim 1, wherein the first set of global word line conductors connects the selected local word line conductors to circuitry in the semiconductor substrate.

4. The memory structure of claim 3, wherein the circuitry in the semiconductor substrate comprises voltage sources.

* * * * *